US006248715B1

(12) United States Patent
Rosenberg et al.

(10) Patent No.: US 6,248,715 B1
(45) Date of Patent: Jun. 19, 2001

(54) METHOD OF TREATING A UROKINASE-TYPE PLASMINOGEN ACTIVATOR-MEDIATED DISORDER

(75) Inventors: Steven Rosenberg, Oakland; Jennifer R. Stratton-Thomas, San Mateo, both of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 08/438,745

(22) Filed: May 10, 1995

Related U.S. Application Data

(60) Division of application No. 08/280,288, filed on Jul. 26, 1994, now abandoned, which is a continuation-in-part of application No. 08/070,153, filed on Jun. 1, 1993, now abandoned.

(51) Int. Cl.$^7$ ............................ A61K 38/00; A61K 38/16
(52) U.S. Cl. ................................... 514/12; 514/2
(58) Field of Search .............................. 514/8, 12, 2, 825

(56) References Cited

U.S. PATENT DOCUMENTS

| | | | |
|---|---|---|---|
| 4,751,180 | 6/1988 | Cousens et al. | 435/68 |
| 4,791,068 | 12/1988 | Loskutoff et al. | 436/518 |
| 4,835,255 | 5/1989 | Weissman et al. | 530/350 |
| 4,880,734 | 11/1989 | Burke et al. | 435/68 |
| 4,999,194 * | 3/1991 | Broeze et al. | 435/215 |
| 5,112,755 | 5/1992 | Heyneker et al. | 435/215 |
| 5,219,569 | 6/1993 | Blaber et al. | 424/94.63 |
| 5,340,833 * | 8/1994 | Bridget et al. | 514/443 |
| 5,376,547 * | 12/1994 | Kalyan et al. | 435/215 |
| 5,389,538 * | 2/1995 | Tanabe et al. | 435/215 |
| 5,416,006 * | 5/1995 | Blasi et al. | 435/215 |

FOREIGN PATENT DOCUMENTS

| | | |
|---|---|---|
| 64187/94 | 10/1994 | (AU) . |
| 69542/94 | 12/1994 | (AU) . |
| WO 86/06100 | 10/1986 | (WO) . |
| WO 92/07083 | 4/1992 | (WO) . |
| WO 94/22464 | 10/1994 | (WO) . |

OTHER PUBLICATIONS

Bowie et al. (1990) Science 247: 1307–1310.*
Ballance et al., "A Hybrid Protein of Urokinase Growth--Factor Domain . . . " *Eur. J. Biochem* 207(1): 177–183.*
Rabbani et al. "Structural Requirements for the Growth Factor Activity . . . " *J. Biol. Chem.* 267(20): 14151–14156, (Jul. 1992).*
Corti et al. "Epitope Mapping of the Anti–Urokinase Monoclonal . . . " *Thromb. Haemostasis* 62(3): 934–939, (Nov. 1989).*
Mazar et al, "Domain Analysis of Urokinase Plasminogen Activator . . . " *Fibrinolysis* 6 (*Suppl. 1*): 49–55, (1992).*
Niedbala et al., "Regulation of Human Squamous Cell Carcimona . . . " *Cancer Comm.* 2(9): 317–324, (Sep. 1990).*
Kobayashi et al., "Saturation of Tumour Cell Surface Receptors . . . " *Br. J. Cancer* 67: 537–544, (Mar., 1993).*
Appella et al., "The Receptor–Binding Sequence of Urokinase" *J. Biol. Chem.* 262(10): 4437–4440, Apr., 1987.
Brake, 1989, "Secretion of Heterologous Proteins Directed by the Yeast α–Factor Leader" *Yeast Genetic Engineering* pp. 269–280.
Schmitt et al., "Fluoescent Probes as Tools to Assess the Receptor for the Urokinase–Type . . . " *Seminars Thromb. Hemo.* 17(3):291–302, Jul., 1991.
Harlow et al., "Antibodies: A Laboratory Marvel" Cold Spring Harbor Laboratory, 1988, p. 513.
Ito et al., "Antibodies Against a Nonapeptide of Polyomarvirus Middle T Antigen: Cross–Reaction with a Cellular Protein(s)" *J. Virol.* 48(3):709–720, Dec., 1983.
Lowman et al., 1991, "Selecting High–Affinity Binding Proteins by Monovalent Phage Display" *Biochemistry* 30:10832–10838.
Matthews et al., 1993, "Substrate Phage: Selection of Protease Substrates by Monovalent Phage Display" *Science* 260:1113–1117.
Nagai et al., 1985, "Molecular Cloning of cDNA Coding for Human Preprourokinase" *Gene* 36:183–186.
Roldan et al., 1990, "Cloning and Expression of the Receptor for Human Urokinase Plasminogen Activator, a Central Molecule of Cell Surface, Plasmin Dependent Proteolysis" *EMBO J.* 9:467–474.
Barr et al., 1989, *Yeast Genetic Engineering* 269–280.
Frederick et al., Mar., 1990, "Glucose Oxidase from *Aspergillus niger*"*J. Biological Chemistry* 265(7):3793–3802.
Kingsman and Kingsman, 1990, Genetic Engineering, Blackwell Scientific Publications.

* cited by examiner

*Primary Examiner*—Michael Pak
(74) *Attorney, Agent, or Firm*—David P. Lenti; Robin L. Teskin; Robert P. Blackburn

(57) ABSTRACT

A method of treating an uPA-mediated disorder is disclosed, which comprises providing and administering an effective amount of polypeptide consisting essentially of the EGF-like domain of human uPA or active analog thereof.

13 Claims, No Drawings

SEQUENCE LISTING

```
(1) GENERAL INFORMATION:

(iii) NUMBER OF SEQUENCES: 22

(2) INFORMATION FOR SEQ ID NO:1:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (xi) SEQUENCE DESCRIPTION: SEQ ID NO:1:

ATGCTAGATC TAATGAACTT CATCAGGTAC CATCG                                 35

(2) INFORMATION FOR SEQ ID NO:2:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (xi) SEQUENCE DESCRIPTION: SEQ ID NO:2:

CGATAGATCT TTATTTTGAC TTATCTATTT CACAG                                 35

(2) INFORMATION FOR SEQ ID NO:3:

(i) SEQUENCE CHARACTERISTICS:
          (A) LENGTH: 953 base pairs
          (B) TYPE: nucleic acid
          (C) STRANDEDNESS: double
          (D) TOPOLOGY: linear (ii) MOLECULE TYPE: cDNA (iii) HYPOTHETICAL: NO
```

-continued (vii) IMMEDIATE SOURCE:
    (B) CLONE: M1Flag-EGF-pIII fusion (ix) FEATURE:
    (A) NAME/KEY: CDS
    (B) LOCATION: 25..903

(xi) SEQUENCE DESCRIPTION: SEQ ID NO:3:

```
CCATGGCTAC AGAGGAATAT TAAA ATG AAT AAG GCA AAA ACT TTA CTC TTC        51
                          Met Asn Lys Ala Lys Thr Leu Leu Phe
                           1               5

ACT GCG CTA GCT TTT GGT TTA TCT CAT CAA GCT TTA GCG GAC TAC AAA        99
Thr Ala Leu Ala Phe Gly Leu Ser His Gln Ala Leu Ala Asp Tyr Lys
 10              15                  20                  25

GAC GAT GAC GAT AAG AAT TCT GAC AGT GAA TGC CCG CTG AGC CAC GAC       147
Asp Asp Asp Asp Lys Asn Ser Asp Ser Glu Cys Pro Leu Ser His Asp
             30                  35                  40

GGC TAC TGC CTG CAC GAC GGT GTT TGC ATG TAC ATC GAA GCT CTA GAC       195
Gly Tyr Cys Leu His Asp Gly Val Cys Met Tyr Ile Glu Ala Leu Asp
             45                  50                  55

AAG TAC GCA TGC AAC TGC GTT GTT GGG TAC ATC GGT GAG CGC TGC CAG       243
Lys Tyr Ala Cys Asn Cys Val Val Gly Tyr Ile Gly Glu Arg Cys Gln
             60                  65                  70

TAC CGA GAT CTT AAG TGG TGG GAA CTC CGT GGG CCC TTC GTT TGT GAA       291
Tyr Arg Asp Leu Lys Trp Trp Glu Leu Arg Gly Pro Phe Val Cys Glu
 75                  80                  85

TAT CAA GGC CAA TCG TCT GAC CTG CCT CAA CCT CCT GTC AAT GCT GGC       339
Tyr Gln Gly Gln Ser Ser Asp Leu Pro Gln Pro Pro Val Asn Ala Gly
 90                  95                 100                 105

GGC GGC TCT GGT GGT GGT TCT GGT GGC GGC TCT GAG GGT GGT GGC TCT       387
Gly Gly Ser Gly Gly Gly Ser Gly Gly Gly Ser Glu Gly Gly Gly Ser
             110                 115                 120

GAG GGT GGC GGT TCT GAG GGT GGC GGC TCT GAG GGA GGC GGT TCC GGT       435
Glu Gly Gly Gly Ser Glu Gly Gly Gly Ser Glu Gly Gly Gly Ser Gly
             125                 130                 135

GGT GGC TCT GGT TCC GGT GAT TTT GAT TAT GAA AAG ATG GCA AAC GCT       483
Gly Gly Ser Gly Ser Gly Asp Phe Asp Tyr Glu Lys Met Ala Asn Ala
             140                 145                 150

AAT AAG GGG GCT ATG ACC GAA AAT GCC GAT GAA AAC GCG CTA CAG TCT       531
Asn Lys Gly Ala Met Thr Glu Asn Ala Asp Glu Asn Ala Leu Gln Ser
 155                 160                 165

GAC GCT AAA GGC AAA CTT GAT TCT GTC GCT ACT GAT TAC GGT GCT GCT       579
Asp Ala Lys Gly Lys Leu Asp Ser Val Ala Thr Asp Tyr Gly Ala Ala
170                 175                 180                 185

ATC GAT GGT TTC ATT GGT GAC GTT TCC GGC CTT GCT AAT GGT AAT GGT       627
Ile Asp Gly Phe Ile Gly Asp Val Ser Gly Leu Ala Asn Gly Asn Gly
             190                 195                 200

GCT ACT GGT GAT TTT GCT GGC TCT AAT TCC CAA ATG GCT CAA GTC GGT       675
Ala Thr Gly Asp Phe Ala Gly Ser Asn Ser Gln Met Ala Gln Val Gly
             205                 210                 215

GAC GGT GAT AAT TCA CCT TTA ATG AAT AAT TTC CGT CAA TAT TTA CCT       723
Asp Gly Asp Asn Ser Pro Leu Met Asn Asn Phe Arg Gln Tyr Leu Pro
             220                 225                 230

TCC CTC CCT CAA TCG GTT GAA TGT CGC CCT TTT GTC TTT AGC GCT GGT       771
Ser Leu Pro Gln Ser Val Glu Cys Arg Pro Phe Val Phe Ser Ala Gly
 235                 240                 245

AAA CCA TAT GAA TTT TCT ATT GAT TGT GAC AAA ATA AAC TTA TTC CGT       819
Lys Pro Tyr Glu Phe Ser Ile Asp Cys Asp Lys Ile Asn Leu Phe Arg
250                 255                 260                 265

GGT GTC TTT GCG TTT CTT TTA TAT GTT GCC ACC TTT ATG TAT GTA TTT       867
Gly Val Phe Ala Phe Leu Leu Tyr Val Ala Thr Phe Met Tyr Val Phe
```

-continued

```
                    270                 275                 280
TCT ACG TTT GCT AAC ATA CTG CGT AAT AAG GAG TCT TAATCATGCG          913
Ser Thr Phe Ala Asn Ile Leu Arg Asn Lys Glu Ser
            285                 290

CGCTCACTGG CCGTCGTTTT ACAACGTCGT GACTGGGAAA                         953
```

(2) INFORMATION FOR SEQ ID NO:4:

(i) SEQUENCE CHARACTERISTICS:
        (A) LENGTH: 293 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asn Lys Ala Lys Thr Leu Leu Phe Thr Ala Leu Ala Phe Gly Leu
 1               5                  10                  15

Ser His Gln Ala Leu Ala Asp Tyr Lys Asp Asp Asp Lys Asn Ser
                20                  25                  30

Asp Ser Glu Cys Pro Leu Ser His Asp Gly Tyr Cys Leu His Asp Gly
            35                  40                  45

Val Cys Met Tyr Ile Glu Ala Leu Asp Lys Tyr Ala Cys Asn Cys Val
    50                  55                  60

Val Gly Tyr Ile Gly Glu Arg Cys Gln Tyr Arg Asp Leu Lys Trp Trp
65                  70                  75                  80

Glu Leu Arg Gly Pro Phe Val Cys Glu Tyr Gln Gly Gln Ser Ser Asp
                85                  90                  95

Leu Pro Gln Pro Pro Val Asn Ala Gly Gly Ser Gly Gly Gly Ser
            100                 105                 110

Gly Gly Gly Ser Glu Gly Gly Ser Glu Gly Gly Ser Glu Gly
        115                 120                 125

Gly Gly Ser Glu Gly Gly Ser Gly Gly Ser Gly Ser Gly Asp
    130                 135                 140

Phe Asp Tyr Glu Lys Met Ala Asn Ala Asn Lys Gly Ala Met Thr Glu
145                 150                 155                 160

Asn Ala Asp Glu Asn Ala Leu Gln Ser Asp Ala Lys Gly Lys Leu Asp
                165                 170                 175

Ser Val Ala Thr Asp Tyr Gly Ala Ala Ile Asp Gly Phe Ile Gly Asp
            180                 185                 190

Val Ser Gly Leu Ala Asn Gly Asn Gly Ala Thr Gly Asp Phe Ala Gly
    195                 200                 205

Ser Asn Ser Gln Met Ala Gln Val Gly Asp Gly Asp Asn Ser Pro Leu
210                 215                 220

Met Asn Asn Phe Arg Gln Tyr Leu Pro Ser Leu Pro Gln Ser Val Glu
225                 230                 235                 240

Cys Arg Pro Phe Val Phe Ser Ala Gly Lys Pro Tyr Glu Phe Ser Ile
                245                 250                 255

Asp Cys Asp Lys Ile Asn Leu Phe Arg Gly Val Phe Ala Phe Leu Leu
            260                 265                 270

Tyr Val Ala Thr Phe Met Tyr Val Phe Ser Thr Phe Ala Asn Ile Leu
        275                 280                 285

Arg Asn Lys Glu Ser
        290
```

(2) INFORMATION FOR SEQ ID NO:5:

(i) SEQUENCE CHARACTERISTICS:
    (A) LENGTH: 953 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (vii) IMMEDIATE SOURCE:
    (B) CLONE: M1Flag-EGF-pIII fusion (ix) FEATURE:
    (A) NAME/KEY: CDS
    (B) LOCATION: 25..903

(xi) SEQUENCE DESCRIPTION: SEQ ID NO:5:

| | | | | | | | | | | | | | | | | |
|---|---|---|---|---|---|---|---|---|---|---|---|---|---|---|---|---|
| CCATGGCTAC AGAGGAATAT TAAA | ATG | AAT | AAG | GCA | AAA | ACT | TTA | CTC | TTC | | | | | | | 51 |
| | Met | Asn | Lys | Ala | Lys | Thr | Leu | Leu | Phe | | | | | | | |
| | 1 | | | | 5 | | | | | | | | | | | |
| ACT | GCG | CTA | GCT | TTT | GGT | TTA | TCT | CAT | CAA | GCT | TTA | GCG | GAC | TAC | AAA | 99 |
| Thr | Ala | Leu | Ala | Phe | Gly | Leu | Ser | His | Gln | Ala | Leu | Ala | Asp | Tyr | Lys | |
| 10 | | | | | 15 | | | | | 20 | | | | | 25 | |
| GAC | GAT | GAC | GAT | AAG | AAT | TCT | GAC | AGT | GAA | TGC | CCG | CTG | AGC | CAC | GAC | 147 |
| Asp | Asp | Asp | Asp | Lys | Asn | Ser | Asp | Ser | Glu | Cys | Pro | Leu | Ser | His | Asp | |
| | | | | 30 | | | | | 35 | | | | | 40 | | |
| GGC | TAC | TGC | CTG | CAC | GAC | GGT | GTT | TGC | ATG | TAC | ATC | GAA | GCT | CTA | GAC | 195 |
| Gly | Tyr | Cys | Leu | His | Asp | Gly | Val | Cys | Met | Tyr | Ile | Glu | Ala | Leu | Asp | |
| | | | 45 | | | | | 50 | | | | | 55 | | | |
| AAG | TAC | GCA | TGC | AAC | TGC | GTT | GTT | GGG | TAC | ATC | GGT | GAG | CGC | TGC | CAG | 243 |
| Lys | Tyr | Ala | Cys | Asn | Cys | Val | Val | Gly | Tyr | Ile | Gly | Glu | Arg | Cys | Gln | |
| | | 60 | | | | | 65 | | | | | 70 | | | | |
| TAC | CGA | GAT | CTT | AAG | TGG | TGG | GAA | CTC | CGT | GGG | CCC | TTC | GTT | TGT | GAA | 291 |
| Tyr | Arg | Asp | Leu | Lys | Trp | Trp | Glu | Leu | Arg | Gly | Pro | Phe | Val | Cys | Glu | |
| | 75 | | | | 80 | | | | | 85 | | | | | | |
| TAT | CAA | GGC | CAA | TCG | TCT | GAC | CTG | CCT | CAA | CCT | CCT | GTC | AAT | GCT | GGC | 339 |
| Tyr | Gln | Gly | Gln | Ser | Ser | Asp | Leu | Pro | Gln | Pro | Pro | Val | Asn | Ala | Gly | |
| 90 | | | | | 95 | | | | | 100 | | | | | 105 | |
| GGC | GGC | TCT | GGT | GGT | GGT | TCT | GGT | GGC | GGC | TCT | GAG | GGT | GGT | GGC | TCT | 387 |
| Gly | Gly | Ser | Gly | Gly | Gly | Ser | Gly | Gly | Gly | Ser | Glu | Gly | Gly | Gly | Ser | |
| | | | | 110 | | | | | 115 | | | | | 120 | | |
| GAG | GGT | GGC | GGT | TCT | GAG | GGT | GGC | GGC | TCT | GAG | GGA | GGC | GGT | TCC | GGT | 435 |
| Glu | Gly | Gly | Gly | Ser | Glu | Gly | Gly | Gly | Ser | Glu | Gly | Gly | Gly | Ser | Gly | |
| | | | 125 | | | | | 130 | | | | | 135 | | | |
| GGT | GGC | TCT | GGT | TCC | GGT | GAT | TTT | GAT | TAT | GAA | AAG | ATG | GCA | AAC | GCT | 483 |
| Gly | Gly | Ser | Gly | Ser | Gly | Asp | Phe | Asp | Tyr | Glu | Lys | Met | Ala | Asn | Ala | |
| | | 140 | | | | | 145 | | | | | 150 | | | | |
| AAT | AAG | GGG | GCT | ATG | ACC | GAA | AAT | GCC | GAT | GAA | AAC | GCG | CTA | CAG | TCT | 531 |
| Asn | Lys | Gly | Ala | Met | Thr | Glu | Asn | Ala | Asp | Glu | Asn | Ala | Leu | Gln | Ser | |
| | 155 | | | | 160 | | | | | 165 | | | | | | |
| GAC | GCT | AAA | GGC | AAA | CTT | GAT | TCT | GTC | GCT | ACT | GAT | TAC | GGT | GCT | GCT | 579 |
| Asp | Ala | Lys | Gly | Lys | Leu | Asp | Ser | Val | Ala | Thr | Asp | Tyr | Gly | Ala | Ala | |
| 170 | | | | 175 | | | | | 180 | | | | | 185 | | |
| ATC | GAT | GGT | TTC | ATT | GGT | GAC | GTT | TCC | GGC | CTT | GCT | AAT | GGT | AAT | GGT | 627 |
| Ile | Asp | Gly | Phe | Ile | Gly | Asp | Val | Ser | Gly | Leu | Ala | Asn | Gly | Asn | Gly | |
| | | | | 190 | | | | | 195 | | | | | 200 | | |
| GCT | ACT | GGT | GAT | TTT | GCT | GGC | TCT | AAT | TCC | CAA | ATG | GCT | CAA | GTC | GGT | 675 |
| Ala | Thr | Gly | Asp | Phe | Ala | Gly | Ser | Asn | Ser | Gln | Met | Ala | Gln | Val | Gly | |
| | | | 205 | | | | | 210 | | | | | 215 | | | |
| GAC | GGT | GAT | AAT | TCA | CCT | TTA | ATG | AAT | AAT | TTC | CGT | CAA | TAT | TTA | CCT | 723 |
| Asp | Gly | Asp | Asn | Ser | Pro | Leu | Met | Asn | Asn | Phe | Arg | Gln | Tyr | Leu | Pro | |
| | | 220 | | | | | 225 | | | | | 230 | | | | |

```
TCC CTC CCT CAA TCG GTT GAA TGT CGC CCT TTT GTC TTT AGC GCT GGT      771
Ser Leu Pro Gln Ser Val Glu Cys Arg Pro Phe Val Phe Ser Ala Gly
        235                 240                 245

AAA CCA TAT GAA TTT TCT ATT GAT TGT GAC AAA ATA AAC TTA TTC CGT      819
Lys Pro Tyr Glu Phe Ser Ile Asp Cys Asp Lys Ile Asn Leu Phe Arg
250                 255                 260                 265

GGT GTC TTT GCG TTT CTT TTA TAT GTT GCC ACC TTT ATG TAT GTA TTT      867
Gly Val Phe Ala Phe Leu Leu Tyr Val Ala Thr Phe Met Tyr Val Phe
                270                 275                 280

TCT ACG TTT GCT AAC ATA CTG CGT AAT AAG GAG TCT TAATCATGCG           913
Ser Thr Phe Ala Asn Ile Leu Arg Asn Lys Glu Ser
            285                 290

CGCTCACTGG CCGTCGTTTT ACAACGTCGT GACTGGGAAA                          953

(2) INFORMATION FOR SEQ ID NO:6:

(i) SEQUENCE CHARACTERISTICS:
        (A) LENGTH: 293 amino acids
        (B) TYPE: amino acid
        (D) TOPOLOGY: linear (ii) MOLECULE TYPE: protein (xi) SEQUENCE DESCRIPTION: SEQ ID NO:6:

Met Asn Lys Ala Lys Thr Leu Leu Phe Thr Ala Leu Ala Phe Gly Leu
 1               5                  10                  15

Ser His Gln Ala Leu Ala Asp Tyr Lys Asp Asp Asp Lys Asn Ser
                20                  25                  30

Asp Ser Glu Cys Pro Leu Ser His Asp Gly Tyr Cys Leu His Asp Gly
            35                  40                  45

Val Cys Met Tyr Ile Glu Ala Leu Asp Lys Tyr Ala Cys Asn Cys Val
        50                  55                  60

Val Gly Tyr Ile Gly Glu Arg Cys Gln Tyr Arg Asp Leu Lys Trp Trp
 65                  70                  75                  80

Glu Leu Arg Gly Pro Phe Val Cys Glu Tyr Gln Gly Gln Ser Ser Asp
                85                  90                  95

Leu Pro Gln Pro Pro Val Asn Ala Gly Gly Gly Ser Gly Gly Gly Ser
                100                 105                 110

Gly Gly Gly Ser Glu Gly Gly Gly Ser Glu Gly Gly Gly Ser Glu Gly
            115                 120                 125

Gly Gly Ser Glu Gly Gly Gly Ser Gly Gly Gly Ser Gly Ser Gly Asp
        130                 135                 140

Phe Asp Tyr Glu Lys Met Ala Asn Ala Asn Lys Gly Ala Met Thr Glu
145                 150                 155                 160

Asn Ala Asp Glu Asn Ala Leu Gln Ser Asp Ala Lys Gly Lys Leu Asp
                165                 170                 175

Ser Val Ala Thr Asp Tyr Gly Ala Ala Ile Asp Gly Phe Ile Gly Asp
            180                 185                 190

Val Ser Gly Leu Ala Asn Gly Asn Gly Ala Thr Gly Asp Phe Ala Gly
        195                 200                 205

Ser Asn Ser Gln Met Ala Gln Val Gly Asp Gly Asp Asn Ser Pro Leu
        210                 215                 220

Met Asn Asn Phe Arg Gln Tyr Leu Pro Ser Leu Pro Gln Ser Val Glu
225                 230                 235                 240

Cys Arg Pro Phe Val Phe Ser Ala Gly Lys Pro Tyr Glu Phe Ser Ile
                245                 250                 255
```

```
Asp Cys Asp Lys Ile Asn Leu Phe Arg Gly Val Phe Ala Phe Leu Leu
            260                 265                 270

Tyr Val Ala Thr Phe Met Tyr Val Phe Ser Thr Phe Ala Asn Ile Leu
        275                 280                 285

Arg Asn Lys Glu Ser
    290
```

(2) INFORMATION FOR SEQ ID NO:7:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vii) IMMEDIATE SOURCE:
        (B) CLONE: EUKMPCR1

(xi) SEQUENCE DESCRIPTION: SEQ ID NO:7:

```
CTCATCAAGC TTTAGCGGAC TACAAAGACG ATGACGATAA GAGCAATGAA CTTCATCAAG    60
```

(2) INFORMATION FOR SEQ ID NO:8:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vii) IMMEDIATE SOURCE:
        (B) CLONE: EUKGPCR1

(xi) SEQUENCE DESCRIPTION: SEQ ID NO:8:

```
CTCATCAAGC TTTAGCCGAA TACATGCCAA TGGAAAGCAA TGAACTTCAT CAAG    54
```

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vii) IMMEDIATE SOURCE:
        (B) CLONE: EUKPCR2

(xi) SEQUENCE DESCRIPTION: SEQ ID NO:9:

```
CACCGGAACC GGATCCACCC TATTTTGACT TATC    34
```

(2) INFORMATION FOR SEQ ID NO:10:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vii) IMMEDIATE SOURCE:
            (B) CLONE: SRO1

(xi) SEQUENCE DESCRIPTION: SEQ ID NO:10:

GAAATAGATA AGTCAAAATA GGGTGGATCC GGTTCCGGTG ATTTTGATTA TG          52

(2) INFORMATION FOR SEQ ID NO:11:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (vii) IMMEDIATE SOURCE:
            (B) CLONE: EUKCPCR1

(xi) SEQUENCE DESCRIPTION: SEQ ID NO:11:

GAAACCATCG ATAGCAGCAC CG                                          22

(2) INFORMATION FOR SEQ ID NO:12:

(i) SEQUENCE CHARACTERISTICS:
            (A) LENGTH: 779 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (vii) IMMEDIATE SOURCE:
            (B) CLONE: M1Flag uPA1-48 - pIII fusion (ix) FEATURE:
            (A) NAME/KEY: CDS
            (B) LOCATION: 25..729

(ix) FEATURE:
            (A) NAME/KEY: AA inserted by suppressor strain
            (B) LOCATION: 79

(xi) SEQUENCE DESCRIPTION: SEQ ID NO:12:

CCATGGCTAC AGAGGAATAT TAAA ATG AAT AAG GCA AAA ACT TTA CTC TTC        51
                          Met Asn Lys Ala Lys Thr Leu Leu Phe
                            1               5

ACT GCG CTA GCT TTT GGT TTA TCT CAT CAA GCT TTA GCC GAC TAC AAA       99
Thr Ala Leu Ala Phe Gly Leu Ser His Gln Ala Leu Ala Asp Tyr Lys
 10              15                  20                  25

GAC GAT GAC GAT AAG AGC AAT GAA CTT CAT CAA GTT CCA TCG AAC TGT      147
Asp Asp Asp Asp Lys Ser Asn Glu Leu His Gln Val Pro Ser Asn Cys
                 30                  35                  40

GAC TGT CTA AAT GGA GGA ACA TGT GTG TCC AAC AAG TAC TTC TCC AAC      195
Asp Cys Leu Asn Gly Gly Thr Cys Val Ser Asn Lys Tyr Phe Ser Asn
             45                  50                  55

ATT CAC TGG TGC AAC TGC CCA AAG AAA TTC GGA GGG CAG CAC TGT GAA      243
Ile His Trp Cys Asn Cys Pro Lys Lys Phe Gly Gly Gln His Cys Glu
         60                  65                  70

ATA GAT AAG TCA AAA TAG GGT GGA TCC GGT TCC GGT GAT TTT GAT TAT      291
Ile Asp Lys Ser Lys Gln Gly Gly Ser Gly Ser Gly Asp Phe Asp Tyr
     75                  80                  85

```
GAA AAG ATG GCA AAC GCT AAT AAG GGG GCT ATG ACC GAA AAT GCC GAT     339
Glu Lys Met Ala Asn Ala Asn Lys Gly Ala Met Thr Glu Asn Ala Asp
 90              95                 100                 105

GAA AAC GCG CTA CAG TCT GAC GCT AAA GGC AAA CTT GAT TCT GTC GCT     387
Glu Asn Ala Leu Gln Ser Asp Ala Lys Gly Lys Leu Asp Ser Val Ala
                 110                 115                 120

ACT GAT TAC GGT GCT GCT ATC GAT GGT TTC ATT GGT GAC GTT TCC GGC     435
Thr Asp Tyr Gly Ala Ala Ile Asp Gly Phe Ile Gly Asp Val Ser Gly
                     125                 130                 135

CTT GCT AAT GGT AAT GGT GCT ACT GGT GAT TTT GCT GGC TCT AAT TCC     483
Leu Ala Asn Gly Asn Gly Ala Thr Gly Asp Phe Ala Gly Ser Asn Ser
             140                 145                 150

CAA ATG GCT CAA GTC GGT GAC GGT GAT AAT TCA CCT TTA ATG AAT AAT     531
Gln Met Ala Gln Val Gly Asp Gly Asp Asn Ser Pro Leu Met Asn Asn
         155                 160                 165

TTC CGT CAA TAT TTA CCT TCC CTC CCT CAA TCG GTT GAA TGT CGC CCT     579
Phe Arg Gln Tyr Leu Pro Ser Leu Pro Gln Ser Val Glu Cys Arg Pro
170                 175                 180                 185

TTT GTC TTT AGC GCT GGT AAA CCA TAT GAA TTT TCT ATT GAT TGT GAC     627
Phe Val Phe Ser Ala Gly Lys Pro Tyr Glu Phe Ser Ile Asp Cys Asp
                 190                 195                 200

AAA ATA AAC TTA TTC CGT GGT GTC TTT GCG TTT CTT TTA TAT GTT GCC     675
Lys Ile Asn Leu Phe Arg Gly Val Phe Ala Phe Leu Leu Tyr Val Ala
             205                 210                 215

ACC TTT ATG TAT GTA TTT TCT ACG TTT GCT AAC ATA CTG CGT AAT AAG     723
Thr Phe Met Tyr Val Phe Ser Thr Phe Ala Asn Ile Leu Arg Asn Lys
         220                 225                 230

GAG TCT TAATCATGCG CGCTCACTGG CCGTCGTTTT ACAACGTCGT GACTGGGAAA     779
Glu Ser
    235

(2) INFORMATION FOR SEQ ID NO:13:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO:13:

Met Asn Lys Ala Lys Thr Leu Leu Phe Thr Ala Leu Ala Phe Gly Leu
  1               5                  10                  15

Ser His Gln Ala Leu Ala Asp Tyr Lys Asp Asp Asp Lys Ser Asn
                 20                  25                  30

Glu Leu His Gln Val Pro Ser Asn Cys Asp Cys Leu Asn Gly Gly Thr
             35                  40                  45

Cys Val Ser Asn Lys Tyr Phe Ser Asn Ile His Trp Cys Asn Cys Pro
         50                  55                  60

Lys Lys Phe Gly Gly Gln His Cys Glu Ile Asp Lys Ser Lys Gln Gly
 65                  70                  75                  80

Gly Ser Gly Ser Gly Asp Phe Asp Tyr Glu Lys Met Ala Asn Ala Asn
                 85                  90                  95

Lys Gly Ala Met Thr Glu Asn Ala Asp Glu Asn Ala Leu Gln Ser Asp
                100                 105                 110

Ala Lys Gly Lys Leu Asp Ser Val Ala Thr Asp Tyr Gly Ala Ala Ile
            115                 120                 125

Asp Gly Phe Ile Gly Asp Val Ser Gly Leu Ala Asn Gly Asn Gly Ala
        130                 135                 140
```

```
Thr Gly Asp Phe Ala Gly Ser Asn Ser Gln Met Ala Gln Val Gly Asp
145                 150                 155                 160

Gly Asp Asn Ser Pro Leu Met Asn Asn Phe Arg Gln Tyr Leu Pro Ser
            165                 170                 175

Leu Pro Gln Ser Val Glu Cys Arg Pro Phe Val Phe Ser Ala Gly Lys
            180                 185                 190

Pro Tyr Glu Phe Ser Ile Asp Cys Asp Lys Ile Asn Leu Phe Arg Gly
            195                 200                 205

Val Phe Ala Phe Leu Leu Tyr Val Ala Thr Phe Met Tyr Val Phe Ser
    210                 215                 220

Thr Phe Ala Asn Ile Leu Arg Asn Lys Glu Ser
225                 230                 235

(2) INFORMATION FOR SEQ ID NO:14:

(i) SEQUENCE CHARACTERISTICS:
        (A) LENGTH: 773 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vii) IMMEDIATE SOURCE:
        (B) CLONE: Glu-tag uPA1-48 - pIII fusion (ix) FEATURE:
        (A) NAME/KEY: CDS
        (B) LOCATION: 25..723

(ix) FEATURE:
        (A) NAME/KEY: AA inserted by suppressor strain
        (B) LOCATION: 77

(xi) SEQUENCE DESCRIPTION: SEQ ID NO:14:

CCATGGCTAC AGAGGAATAT TAAA ATG AAT AAG GCA AAA ACT TTA CTC TTC            51
                          Met Asn Lys Ala Lys Thr Leu Leu Phe
                            1               5

ACT GCG CTA GCT TTT GGT TTA TCT CAT CAA GCT TTA GCC GAA TAC ATG           99
Thr Ala Leu Ala Phe Gly Leu Ser His Gln Ala Leu Ala Glu Tyr Met
 10              15                  20                  25

CCA ATG GAA AGC AAT GAA CTT CAT CAA GTT CCA TCG AAC TGT GAC TGT          147
Pro Met Glu Ser Asn Glu Leu His Gln Val Pro Ser Asn Cys Asp Cys
             30                  35                  40

CTA AAT GGA GGA ACA TGT GTG TCC AAC AAG TAC TTC TCC AAC ATT CAC          195
Leu Asn Gly Gly Thr Cys Val Ser Asn Lys Tyr Phe Ser Asn Ile His
         45                  50                  55

TGG TGC AAC TGC CCA AAG AAA TTC GGA GGG CAG CAC TGT GAA ATA GAT          243
Trp Cys Asn Cys Pro Lys Lys Phe Gly Gly Gln His Cys Glu Ile Asp
     60                  65                  70

AAG TCA AAA TAG GGT GGA TCC GGT TCC GGT GAT TTT GAT TAT GAA AAG          291
Lys Ser Lys Gln Gly Gly Ser Gly Ser Gly Asp Phe Asp Tyr Glu Lys
 75                  80                  85

ATG GCA AAC GCT AAT AAG GGG GCT ATG ACC GAA AAT GCC GAT GAA AAC          339
Met Ala Asn Ala Asn Lys Gly Ala Met Thr Glu Asn Ala Asp Glu Asn
 90                  95                 100                 105

GCG CTA CAG TCT GAC GCT AAA GGC AAA CTT GAT TCT GTC GCT ACT GAT          387
Ala Leu Gln Ser Asp Ala Lys Gly Lys Leu Asp Ser Val Ala Thr Asp
                110                 115                 120

TAC GGT GCT GCT ATC GAT GGT TTC ATT GGT GAC GTT TCC GGC CTT GCT          435
Tyr Gly Ala Ala Ile Asp Gly Phe Ile Gly Asp Val Ser Gly Leu Ala
```

-continued

```
                      125                 130                 135
AAT GGT AAT GGT GCT ACT GGT GAT TTT GCT GGC TCT AAT TCC CAA ATG        483
Asn Gly Asn Gly Ala Thr Gly Asp Phe Ala Gly Ser Asn Ser Gln Met
            140                 145                 150

GCT CAA GTC GGT GAC GGT GAT AAT TCA CCT TTA ATG AAT AAT TTC CGT        531
Ala Gln Val Gly Asp Gly Asp Asn Ser Pro Leu Met Asn Asn Phe Arg
    155                 160                 165

CAA TAT TTA CCT TCC CTC CCT CAA TCG GTT GAA TGT CGC CCT TTT GTC        579
Gln Tyr Leu Pro Ser Leu Pro Gln Ser Val Glu Cys Arg Pro Phe Val
170                 175                 180                 185

TTT AGC GCT GGT AAA CCA TAT GAA TTT TCT ATT GAT TGT GAC AAA ATA        627
Phe Ser Ala Gly Lys Pro Tyr Glu Phe Ser Ile Asp Cys Asp Lys Ile
            190                 195                 200

AAC TTA TTC CGT GGT GTC TTT GCG TTT CTT TTA TAT GTT GCC ACC TTT        675
Asn Leu Phe Arg Gly Val Phe Ala Phe Leu Leu Tyr Val Ala Thr Phe
                205                 210                 215

ATG TAT GTA TTT TCT ACG TTT GCT AAC ATA CTG CGT AAT AAG GAG TCT        723
Met Tyr Val Phe Ser Thr Phe Ala Asn Ile Leu Arg Asn Lys Glu Ser
            220                 225                 230

TAATCATGCG CGCTCACTGG CCGTCGTTTT ACAACGTCGT GACTGGGAAA                 773
```

(2) INFORMATION FOR SEQ ID NO:15:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO:15:

```
Met Asn Lys Ala Lys Thr Leu Leu Phe Thr Ala Leu Ala Phe Gly Leu
 1               5                  10                  15

Ser His Gln Ala Leu Ala Glu Tyr Met Pro Met Glu Ser Asn Glu Leu
                20                  25                  30

His Gln Val Pro Ser Asn Cys Asp Cys Leu Asn Gly Gly Thr Cys Val
            35                  40                  45

Ser Asn Lys Tyr Phe Ser Asn Ile His Trp Cys Asn Cys Pro Lys Lys
        50                  55                  60

Phe Gly Gly Gln His Cys Glu Ile Asp Lys Ser Lys Gln Gly Gly Ser
65                  70                  75                  80

Gly Ser Gly Asp Phe Asp Tyr Glu Lys Met Ala Asn Ala Asn Lys Gly
                85                  90                  95

Ala Met Thr Glu Asn Ala Asp Glu Asn Ala Leu Gln Ser Asp Ala Lys
                100                 105                 110

Gly Lys Leu Asp Ser Val Ala Thr Asp Tyr Gly Ala Ala Ile Asp Gly
            115                 120                 125

Phe Ile Gly Asp Val Ser Gly Leu Ala Asn Gly Asn Gly Ala Thr Gly
    130                 135                 140

Asp Phe Ala Gly Ser Asn Ser Gln Met Ala Gln Val Gly Asp Gly Asp
145                 150                 155                 160

Asn Ser Pro Leu Met Asn Asn Phe Arg Gln Tyr Leu Pro Ser Leu Pro
                165                 170                 175

Gln Ser Val Glu Cys Arg Pro Phe Val Phe Ser Ala Gly Lys Pro Tyr
                180                 185                 190

Glu Phe Ser Ile Asp Cys Asp Lys Ile Asn Leu Phe Arg Gly Val Phe
            195                 200                 205
```

```
Ala Phe Leu Leu Tyr Val Ala Thr Phe Met Tyr Val Phe Ser Thr Phe
    210                 215                 220

Ala Asn Ile Leu Arg Asn Lys Glu Ser
225                 230

(2) INFORMATION FOR SEQ ID NO:16:

(i) SEQUENCE CHARACTERISTICS:
        (A) LENGTH: 773 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vii) IMMEDIATE SOURCE:
         (B) CLONE: Glu-tag uPA1-48 synth. - pIII map (ix) FEATURE:
         (A) NAME/KEY: CDS
         (B) LOCATION: 25..723

(ix) FEATURE:
         (A) NAME/KEY: AA inserted by suppressor strain
         (B) LOCATION: 77

(xi) SEQUENCE DESCRIPTION: SEQ ID NO:16:
```

```
CCATGGCTAC AGAGGAATAT TAAA ATG AAT AAG GCA AAA ACT TTA CTC TTC        51
                          Met Asn Lys Ala Lys Thr Leu Leu Phe
                           1               5

ACT GCG CTA GCT TTT GGT TTA TCT CAT CAA GCT TTA GCG GAA TAC ATG       99
Thr Ala Leu Ala Phe Gly Leu Ser His Gln Ala Leu Ala Glu Tyr Met
 10              15                  20                  25

CCA ATG GAA AGC AAT GAG CTC CAT CAA GTA CCA TCG AAC TGT GAC TGT      147
Pro Met Glu Ser Asn Glu Leu His Gln Val Pro Ser Asn Cys Asp Cys
                 30                  35                  40

CTA AAT GGA GGT ACC TGT GTG TCC AAC AAG TAC TTT TCG AAC ATT CAC      195
Leu Asn Gly Gly Thr Cys Val Ser Asn Lys Tyr Phe Ser Asn Ile His
             45                  50                  55

TGG TGC AAT TGC CCA AAG AAA TTC GGA GGG CAG CAC TGT GAA ATC GAT      243
Trp Cys Asn Cys Pro Lys Lys Phe Gly Gly Gln His Cys Glu Ile Asp
         60                  65                  70

AAG TCA AAA TAG GGT GGA TCC GGT TCC GGT GAT TTT GAT TAT GAA AAG      291
Lys Ser Lys Gln Gly Gly Ser Gly Ser Gly Asp Phe Asp Tyr Glu Lys
     75                  80                  85

ATG GCA AAC GCT AAT AAG GGG GCT ATG ACC GAA AAT GCC GAT GAA AAC      339
Met Ala Asn Ala Asn Lys Gly Ala Met Thr Glu Asn Ala Asp Glu Asn
 90                  95                 100                 105

GCG CTA CAG TCT GAC GCT AAA GGC AAA CTT GAT TCT GTC GCT ACT GAT      387
Ala Leu Gln Ser Asp Ala Lys Gly Lys Leu Asp Ser Val Ala Thr Asp
                110                 115                 120

TAC GGT GCT GCT ATC GAT GGT TTC ATT GGT GAC GTT TCC GGC CTT GCT      435
Tyr Gly Ala Ala Ile Asp Gly Phe Ile Gly Asp Val Ser Gly Leu Ala
            125                 130                 135

AAT GGT AAT GGT GCT ACT GGT GAT TTT GCT GGC TCT AAT TCC CAA ATG      483
Asn Gly Asn Gly Ala Thr Gly Asp Phe Ala Gly Ser Asn Ser Gln Met
        140                 145                 150

GCT CAA GTC GGT GAC GGT GAT AAT TCA CCT TTA ATG AAT AAT TTC CGT      531
Ala Gln Val Gly Asp Gly Asp Asn Ser Pro Leu Met Asn Asn Phe Arg
    155                 160                 165

CAA TAT TTA CCT TCC CTC CCT CAA TCG GTT GAA TGT CGC CCT TTT GTC      579
Gln Tyr Leu Pro Ser Leu Pro Gln Ser Val Glu Cys Arg Pro Phe Val
170                 175                 180                 185
```

```
TTT AGC GCT GGT AAA CCA TAT GAA TTT TCT ATT GAT TGT GAC AAA ATA        627
Phe Ser Ala Gly Lys Pro Tyr Glu Phe Ser Ile Asp Cys Asp Lys Ile
            190                 195                 200

AAC TTA TTC CGT GGT GTC TTT GCG TTT CTT TTA TAT GTT GCC ACC TTT        675
Asn Leu Phe Arg Gly Val Phe Ala Phe Leu Leu Tyr Val Ala Thr Phe
            205                 210                 215

ATG TAT GTA TTT TCT ACG TTT GCT AAC ATA CTG CGT AAT AAG GAG TCT        723
Met Tyr Val Phe Ser Thr Phe Ala Asn Ile Leu Arg Asn Lys Glu Ser
            220                 225                 230

TAATCATGCG CGCTCACTGG CCGTCGTTTT ACAACGTCGT GACTGGGAAA                  773
```

(2) INFORMATION FOR SEQ ID NO:17:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO:17:

```
Met Asn Lys Ala Lys Thr Leu Leu Phe Thr Ala Leu Ala Phe Gly Leu
 1               5                  10                  15

Ser His Gln Ala Leu Ala Glu Tyr Met Pro Met Glu Ser Asn Glu Leu
                20                  25                  30

His Gln Val Pro Ser Asn Cys Asp Cys Leu Asn Gly Thr Cys Val
                35                  40                  45

Ser Asn Lys Tyr Phe Ser Asn Ile His Trp Cys Asn Cys Pro Lys Lys
                50                  55                  60

Phe Gly Gly Gln His Cys Glu Ile Asp Lys Ser Lys Gln Gly Gly Ser
 65                  70                  75                  80

Gly Ser Gly Asp Phe Asp Tyr Glu Lys Met Ala Asn Ala Asn Lys Gly
                85                  90                  95

Ala Met Thr Glu Asn Ala Asp Glu Asn Ala Leu Gln Ser Asp Ala Lys
                100                 105                 110

Gly Lys Leu Asp Ser Val Ala Thr Asp Tyr Gly Ala Ala Ile Asp Gly
                115                 120                 125

Phe Ile Gly Asp Val Ser Gly Leu Ala Asn Gly Asn Gly Ala Thr Gly
                130                 135                 140

Asp Phe Ala Gly Ser Asn Ser Gln Met Ala Gln Val Gly Asp Gly Asp
145                 150                 155                 160

Asn Ser Pro Leu Met Asn Asn Phe Arg Gln Tyr Leu Pro Ser Leu Pro
                165                 170                 175

Gln Ser Val Glu Cys Arg Pro Phe Val Phe Ser Ala Gly Lys Pro Tyr
                180                 185                 190

Glu Phe Ser Ile Asp Cys Asp Lys Ile Asn Leu Phe Arg Gly Val Phe
                195                 200                 205

Ala Phe Leu Leu Tyr Val Ala Thr Phe Met Tyr Val Phe Ser Thr Phe
                210                 215                 220

Ala Asn Ile Leu Arg Asn Lys Glu Ser
225                 230
```

(2) INFORMATION FOR SEQ ID NO:18:

(i) SEQUENCE CHARACTERISTICS:
        (A) LENGTH: 39 base pairs
        (B) TYPE: nucleic acid
        (C) STRANDEDNESS: single (D) TOPOLOGY: linear (ii) MOLECULE TYPE: cDNA (iii) HYPOTHETICAL: NO (vii) IMMEDIATE SOURCE:
                (B) CLONE: SRO35

(xi) SEQUENCE DESCRIPTION: SEQ ID NO:18:

AGCTTTAGCG GAATACATGC CAATGGAAAG CAATGAGCT                                           39

(2) INFORMATION FOR SEQ ID NO:19:

(i) SEQUENCE CHARACTERISTICS:
                (A) LENGTH: 31 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (vii) IMMEDIATE SOURCE:
                (B) CLONE: SRO36

(xi) SEQUENCE DESCRIPTION: SEQ ID NO:19:

CATTGCTTTC CATTGGCATG TATTCCGCTA A                                                   31

(2) INFORMATION FOR SEQ ID NO:20:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (vii) IMMEDIATE SOURCE:
                (B) CLONE: SRO37

(xi) SEQUENCE DESCRIPTION: SEQ ID NO:20:

CGATAAGTCA AAATAGGGTG                                                                20

(2) INFORMATION FOR SEQ ID NO:21:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (vii) IMMEDIATE SOURCE:
                (B) CLONE: SRO38

(xi) SEQUENCE DESCRIPTION: SEQ ID NO:21:

GATCCACCCT ATTTTGACTT AT                                                             22

(2) INFORMATION FOR SEQ ID NO:22:

(i) SEQUENCE CHARACTERISTICS:
                (A) LENGTH: 48 amino acids
                (B) TYPE: amino acid

```
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Homo sapiens (xi) SEQUENCE DESCRIPTION: SEQ ID NO:22:

Ser Asn Glu Leu His Gln Val Pro Ser Asn Cys Asp Cys Leu Asn Gly
1               5                  10                 15

Gly Thr Cys Val His Gln Val Pro Ser Asn Cys Asp Cys Leu Asn Gly
            20                  25                 30

Gly Thr Cys Val Ser Asn Lys Tyr Phe Ser Asn Ile His Trp Cys Asn
            35                  40                 45
```

METHOD OF TREATING A UROKINASE-TYPE PLASMINOGEN ACTIVATOR-MEDIATED DISORDER

RELATED APPLICATIONS

This application is a divisional of U.S. Ser. No. 08/280,288, filed Jul. 26, 1994, now abandoned, which is a continuation of U.S. Ser. No. 08/070,153, filed Jun. 1, 1993 now abandoned.

DESCRIPTION

1. Technical Field

This invention relates to the fields of cellular biology and protein expression. More particularly, the invention relates to peptide ligands of the urokinase plasminogen activator receptor, and methods for preparing the same.

2. Background of the Invention

Urokinase-type plasminogen activator (uPA) is a multi-domain serine protease, having a catalytic "B" chain (amino acids 144–411), and an amino-terminal fragment ("ATF", aa 1–143) consisting of a growth factor-like domain (4–43) and a kringle (aa 47–135). The uPA kringle appears to bind heparin, but not fibrin, lysine, or aminohex-anoic acid. The growth factor-like domain bears some similarity to the structure of epidermal growth factor (EGF), and is thus also referred to as an "EGF-like" domain. The single chain pro-uPA is activated by plasmin, cleaving the chain into the two chain active form, which is linked together by a disulfide bond.

uPA binds to its specific cell surface receptor (uPAR). The binding interaction is apparently mediated by the EGF-like domain (S. A. Rabbani et al., *J Biol Chem* (1992) 267:14151–56). Cleavage of pro-uPA into active uPA is accelerated when pro-uPA and plasminogen are receptor-bound. Thus, plasmin activates pro-uPA, which in turn activates more plasmin by cleaving plasminogen. This positive feedback cycle is apparently limited to the receptor-based proteolysis on the cell surface, since a large excess of protease inhibitors is found in plasma, including $\alpha_2$ antiplasmin, PAI-1 and PAI-2.

Plasmin can activate or degrade extracellular proteins such as fibrinogen, fibronectin, and zymogens. Plasminogen activators thus can regulate extracellular proteolysis, fibrin clot lysis, tissue remodeling, developmental cell migration, inflammation, and metastasis. Accordingly, there is great interest in developing uPA inhibitors and uPA receptor antagonists. E. Appella et al., *J Biol Chem* (1987) 262:4437–40 determined that receptor binding activity is localized in the EGF-like domain, and that residues 12–32 appear to be critical for binding. The critical domain alone ($uPA_{12-32}$) bound uPAR with an affinity of 40 nM (about 100 fold less than intact ATF).

S. A. Rabbani et al., supra, disclosed that the EGF-like domain is fucosylated at $Thr_{18}$, and reported that fucosylated EGF-like domain ($uPA_{4-43}$, produced by cleavage from pro-uPA) was mitogenic for an osteosarcoma cell line, SaOS-2. In contrast, non-fucosylated EGF-like domain bound uPAR with an affinity equal to the fucosylated EGF-like domain, but exhibited no mitogenic activity. Non-fucosylated EGF-like domain competed for binding to uPAR with fucosylated EGF-like domain, and reduced the mitogenic activity observed. Neither EGF-like domain was mitogenic in U937 fibroblast cells.

Previously, it was suggested that an "epitope library" might be made by cloning synthetic DNA that encodes random peptides into filamentous phage vectors (Parmley and Smith, *Gene* (1988) 73:305). It was proposed that the synthetic DNA be cloned into the coat protein gene III because of the likelihood of the encoded peptide becoming part of pIII without significantly interfering with pIII's function. It is known that the amino terminal half of pIII binds to the F pilus during infection of the phage into *E. coli*. It was suggested that such phage that carry and express random peptides on their cell surface as part of pIII may provide a way of identifying the epitopes recognized by antibodies, particularly using antibody to affect the purification of phage from the library. Devlin, PCT WO91/18980 (incorporated herein by reference) described a method for producing a library consisting of random peptide sequences presented on filamentous phage. The library can be used for many purposes, including identifying and selecting peptides that have a particular bioactivity. An example of a ligand binding molecule would be a soluble or insoluble cellular receptor (i.e., a membrane bound receptor), but would extend to virtually any molecule, including enzymes, that have the sought after binding activity. Description of a similar library is found in Dower et al., WO91/19818. The present invention provides a method for screening such libraries (and other libraries of peptides) to determine bioactive peptides or compounds. Kang et al., WO92/18619 disclosed a phage library prepared by inserting into the pvIII gene.

However, both the pIII and pVIII proteins are expressed in multiple copies in filamentous bacteriophage. As a result, the phage are selected and amplified based on their avidity for the target, rather than their affinity. To overcome this problem, a method for monovalent (only one test peptide per phage) phage display has been developed (H. B. Lowman et al., *Biochem* (1991) 30:10832–38). To obtain monovalent display, the bacterial host is coinfected with the phage library and a large excess of "helper" phage, which express only wild-type pIII (and/or pVIII) and are inefficiently packaged. By adjusting the ratio of display phage to helper phage, one can adjust the ratio of modified to wild-type display proteins so that most phage have only one modified protein. However, this results in a large amount of phage having only wild-type pIII (or pVIII), which significantly raises the background noise of the screening.

DISCLOSURE OF THE INVENTION

One aspect of the invention is a method for producing non-fucosylated uPA EGF-like domain, particularly $uPA_{1-48}$.

Another aspect of the invention is non-fucosylated $uPA_{1-48}$, which is useful for inhibiting the mitogenic activity of uPA in cancer cells.

Another aspect of the invention is a method for treating cancer and metastasis by administering an effective amount of a non-fucosylated uPA EGF-like domain, particularly $uPA_{1-48}$.

Another aspect of the invention is a method treating a uPA-mediated disorder by administering a composition comprising an effective amount of a non-fucosylated polypeptide consisting of the EDF-like domain by instillation in the eye.

Another aspect of the invention is a method for pre-enriching a monovalent phage display mixture prior to screening for binding to a target, by providing a mixture of monovalent display phage and non-displaying phage, wherein the monovalent display phage display both a candidate peptide and a common peptide, the common peptide is identical for each monovalent display phage, and the candidate peptide is different for different monovalent display phage; and separating all phage displaying the common peptide from phage not displaying a common peptide.

MODES OF CARRYING OUT THE INVENTION

A. Definitions

The term "huPA" refers specifically to human urokinase-type plasminogen activator. The "EGF-like domain" is that portion of the huPA molecule responsible for mediating huPA binding to its receptor (uPAR). The EGF-like domain, sometimes called the growth factor-like domain ("GFD"), is located within the first 48 residues of huPA. The critical residues (essential for binding activity) have been localized to positions 12–32, although a peptide containing only those residues does not exhibit a binding affinity high enough to serve as a useful receptor antagonist.

The term "huPAR antagonist polypeptide" refers to a polypeptide having a sequence identical to the EGF-like domain of huPA (residues 1–48), or an active portion thereof. An "active portion" is one which lacks up to 10 amino acids, from the N-terminal or C-terminal ends, or a combination thereof, of the huPA$_{1-48}$ polypeptide, and exhibits a $K_d \leq 5$ nM with huPAR. The term "active analog" refers to a polypeptide differing from the sequence of the EGF-like domain of huPA$_{1-48}$ or an active portion thereof by 1–7 amino acids, but which still exhibits a $K_d \leq 5$ nM with huPAR. The differences are preferably conservative amino acid substitutions, in which an amino acid is replaced with another natually-occurring amino acid of similar character. For example, the following substitutions are considered "conservative": Gly↔Ala; Val↔Ile↔Leu; Asp↔Glu; Lys↔Arg; Asn↔Gln; and Phe↔Trp↔Tyr. Nonconservative changes are generally substitutions of one of the above amino acids with an amino acid from a different group (e.g., substituting Asn for Glu), or substituting Cys, Met, His, or Pro for any of the above amino acids. The huPAR antagonist polypeptides of the invention should be substantially free of peptides derived from other portions of the huPA protein. For example, a huPAR antagonist composition should contain less than 20 wt % uPA B domain (dry weight, absent excipients), preferably less than 10 wt % uPA-B, more preferably less than 5 wt % uPA-B, most preferably no detectable amount. The huPAR antagonist polypeptides also preferably exclude the kringle region of uPA.

The term "expression vector" refers to an oligonucleotide which encodes the huPAR antagonist polypeptide of the invention and provides the sequences necessary for its expression in the selected host cell. Expression vectors will generally include a transcriptional promoter and terminator, or will provide for incorporation adjacent to an endogenous promoter. Expression vectors will usually be plasmids, further comprising an origin of replication and one or more selectable markers. However, expression vectors may alternatively be viral recombinants designed to infect the host, or integrating vectors designed to integrate at a preferred site within the host's genome. Expression vectors may further comprise an oligonucleotide encoding a signal leader polypeptide. When "operatively connected", the huPAR antagonist is expressed downstream and in frame with the signal leader, which then provides for secretion of the huPAR antagonist polypeptide by the host to the extracellular medium. Presently preferred signal leaders are the Saccharomyces cerevisiae α-factor leader (particularly when modified to delete extraneous Glu-Ala sequences), and the ubiquitin leader (for intracellular expression).

The term "transcriptional promoter" refers to an oligonucleotide sequence which provides for regulation of the DNA→mRNA transcription process, typically based on temperature, or the presence or absence of metabolites, inhibitors, or inducers. Transcriptional promoters may be regulated (inducible/repressible) or constitutive. Yeast glycolytic enzyme promoters are capable of driving the transcription and expression of heterologous proteins to high levels, and are particularly preferred. The presently preferred promoter is the hybrid ADH2/GAP promoter described in Tekamp-Olson et al., U.S. Pat. No. 4,876,197 (incorporated herein by reference), comprising the S. cerevisiae glyceralde-hyde-3-phosphate dehydrogenase promoter in combination with the S. cerevisiae alcohol dehydrogenase II upstream activation site.

The term "host" refers to a yeast cell suitable for expressing heterologous polypeptides. There are a variety of suitable genera, such as Saccharomyces, Schizosaccharomyces, Kluveromyces, Pichia, Hansenula, and the like. Presently preferred are yeast of the Saccharomyces genus, particularly Saccharomyces cerevisiae.

The term "uPA-mediated disorder" refers to a disease state or malady which is caused or exacerbated by a biological activity of uPA. The primnary biological activity exhibited is plasminogen activation. Disorders mediated by plasminogen activation include, without limitation, inappropriate angiogenesis (e.g., diabetic retinopathy, corneal angiogenesis, Kaposi's sarcoma, and the like), metastasis and invasion by tumor cells, and chronic inflammation (e.g., rheumatoid arthritis, emphysema, and the like). Fucosylaied ATF is also mitogenic for some tumor cells (e.g., SaOS-2 osteosar-coma cells), which sometimes self-activate in an autocrine mechanism. Accordingly, the huPAR antagonist of the invention is effective in inhibiting the proliferation of uPA-activated tumor cells.

The term "effective amount" refers to an amount of huPAR antagonist polypeptide sufficient to exhibit a detectable therapeutic effect. The therapeutic effect may include, for example, without limitation, inhibiting the growth of undesired tissue or malignant cells, inhibiting inappropriate angiogenesis, limiting tissue damage caused by chronic inflammation, and the like. The precise effective amount for a subject will depend upon the subject's size and health, the nature and severity of the condition to be treated, and the like. Thus, it is not possible to specify an exact effective amount in advance. However, the effective amount for a given situation can be determined by routine experimentation based on the information provided herein.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

The term "pre-enriching" refers to increasing the concentration of candidate phage in a monovalent phage display mixture by removing phage which do not have a candidate peptide. A "monovalent phage display mixture" is a mixture of phage containing recombinant phage and helper phage in a ratio such that most phage display at most one recombinant surface protein.

The term "common peptide" refers to a distinctive heterologous (not wild-type) peptide sequence which is displayed identically by all recombinant members of a phage (or other host) library. The common peptide is preferably an epitope recognized by a high-affinity antibody, which is not cross-reactive with any epitopes naturally occurring in the wild-type phage. The common peptide permits one to select all recombinant phage (having a common peptide and a random candidate peptide) as a set, and purify them away from non-recombinant (wild-type) phage. The presently preferred common peptide is Glu-Tyr-Met-Pro-Met-Glu.

B. General Method

The present invention relies on the fact that yeast do not fucosylate proteins upon expression, but are able to express properly folded, active uPA and fragments. One may employ other eukaryotic hosts in the practice of the invention as long as the host is incapable of fucosylating proteins, whether naturally or due to manipulation (e.g., genetic mutation or antibiotic treatment). Presently preferred hosts are yeasts, particularly Saccharomyces, Schizosaccharomyces, Kluveromyces, Pichia, Hansenula, and the like, especially *S. cerevisiae*. Strains AB110 and MB2-1 are presently preferred.

The expression vector is constructed according to known methods, and typically comprises a plasmid functional in the selected host. The uPA sequence used may be cloned following the method described in Example 1 below. Variations thereof (i.e., active fragments and active analogs) may be generated by site-specific mutagenesis, imperfect PCR, and other methods known in the art. Stable plasmids generally require an origin of replication (such as the yeast $2\mu$ ori), and one or more selectable markers (such as antibiotic resistance) which can be used to screen for transformants and force retention of the plasmid. The vector should provide a promoter which is functional in the selected host cell, preferably a promoter derived from yeast glycolytic enzyme promoters such as GAPDH, GAL, and ADH2. These promoters are highly efficient, and can be used to drive expression of heterologous proteins up to about 10% of the host cell weight. The presently preferred promoter is a hybrid ADH2/GAP promoter comprising the *S. cerevisiae* glyceraldehyde-3-phosphate dehydrogenase promoter in combination with the *S. cerevisiae* alcohol dehydrogenase II upstream activation site.

The expression vector should ideally provide a signal leader sequence between the promoter and the huPAR antagonist polypeptide sequence. The signal leader sequence provides for translocation of the huPAR antagonist polypeptide through the endoplasmic reticulum and export from the cell into the extracellular medium, where it may be easily harvested. There are a number of signal leader sequences known that are functional in yeast. The yeast α-factor leader is presently preferred (see U.S. Pat. No. 4,751,180, incorporated herein by reference).

Alternatively, the vector may provide for integration into the host genome, as is described by Shuster, PCT WO92/01800, incorporated herein by reference.

Transformations into yeast can be carried out according to the method of A. Hinnen et al., *Proc Natl Acad Sci USA* (1978) 75:1929–33, or H. Ito et al., *J Bacteriol* (1983) 153:163–68. After DNA is taken up by the host cell, the vector integrates into the yeast genome at one or more sites homologous to its targeting sequence. It is presently preferred to linearize the vector by cleaving it within the targeting sequence using a restriction endonuclease, as this procedure increases the efficiency of integration.

Following successful transformations, the number of integrated sequences may be increased by classical genetic techniques. As the individual cell clones can carry integrated vectors at different locations, a genetic cross between two appropriate strains followed by sporulation and recovery of segregants can result in a new yeast strain having the integrated sequences of both original parent strains. Continued cycles of this method with other integratively transformed strains can be used to further increase the copies of integrated plasmids in a yeast host strain. One may also amplify the integrated sequences by standard techniques, for example by treating the cells with increasing concentrations of copper ions (where a gene for copper resistance has been included in the integrating vector).

Correct ligations for plasmid construction may be confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the plasmid construction, as is understood in the art. Plasmids from the transformants are then prepared according to the method of D. B. Clewell et al., *Proc Natl Acad Sci USA* (1969) 62:1159, optionally following chloramphenicol amplification (D. B. Clewell, *J Bacteriol* (1972) 110:667). Isolated DNA is analyzed by restriction mapping and/or sequenced by the dideoxy method of F. Sanger et al., *Proc Natl Acad Sci USA* (1977) 74:5463 as further described by Messing et al., *Nucl Acids Res* (1981) 9:309, or by the method of Maxam and Gilbert, *Meth Enzymol* (1980) 65:499.

huPAR antagonist polypeptides may be assayed for activity by methods known in the art. For example, one may assay competition of the antagonist against native uPA for cell surface receptor binding. Competition for the receptor correlates with inhibition of uPA biological activity. One may assay huPAR antagonist polypeptides for antimitogenic activity on appropriate tumor cell lines, such as the osteosarcoma cell line SaOS-2 described in the art. Inhibition of mitogenic activity may be determined by comparing the uptake of $^3$H-T in osteosarcoma cells treated with the antagonist against controls. One may also assay huPAR antagonists for anti-invasive activity on appropriate tumor cell lines, such as HOC-1 and HCT116 (W. Schlechte et al., *Cancer Comm* (1990) 2:173–79; H. Kobayashi et al., *Brit J Cancer* (1993) 67:537–44).

huPAR antagonists are administered orally, topically, or by parenteral means, including subcutaneous and intramuscular injection, implantation of sustained release depots, intravenous injection, intranasal administration, and the like. When used to treat tumors, it may be advantageous to apply the huPAR antagonist directly to the site, e.g., during surgery to remove the bulk of the tumor. Accordingly, huPAR antagonist may be administered as a pharmaceutical composition comprising huPAR antagonist in combination with a pharmaceutically acceptable excipient. Such compositions may be aqueous solutions, emulsions, creams, ointments, suspensions, gels, liposomal suspensions, and the like. Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, and other wound dressings. Alternatively, one may incorporate or encapsulate the huPAR antagonist in a suitable polymer matrix or membrane, thus providing a sustained-release delivery device suitable for implantation near the site to be treated locally. Other devices include indwelling catheters and devices such as the Alzet® minipump. Ophthalmic preparations may be formulated using commercially available vehicles such as Sorbi-care® (Allergan), Neodecadron® (Merck, Sharp & Dohme), Lacrilube®, and the like, or may employ topical preparations such as that described in U.S. Pat. No. 5,124,155, incorporated herein by reference. Further, one may provide a huPAR antagonist in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.).

The amount of huPAR antagonist required to treat any particular disorder will of course vary depending upon the nature and severity of the disorder, the age and condition of the subject, and other factors readily determined by one of ordinary skill in the art. The appropriate dosage may be determined by one of ordinary skill by following the methods set forth below in the examples. As a general guide, about 0.01 mg/Kg to about 50 mg/Kg huPAR antagonist administered i.v. or subcutaneously is effective for inhibiting tissue damage due to chronic inflammation. For treating corneal angiogenesis, huPAR antagonist may be administered locally in a gel or matrix at a concentration of about 0.001 mg/Kg to about 5 mg/Kg.

C. EXAMPLES

The examples presented below are provided as a further guide to the practitioner of ordinary skill in the art, and are not to be construed as limiting the invention in any way.

Example 1

(Cloning and Expression of $huPA_{1-48}$)

DNA encoding residues 1–48 of mature human uPA (huPA) was cloned into a yeast expression vector as a fusion with the yeast alpha-factor leader (αFl), under transcriptional control of a hybrid ADH2-GAP promoter. The αFl is described in Brake, U.S. Pat. No. 4,870,008, incorporated herein by reference. The hybrid ADH2-GAP promoter is described in Tekamp-Olson et al., U.S. Pat. No. 4,876,197, and Tekamp-Olson et al., U.S. Pat. No. 4,880,734, both incorporated herein by reference.

The gene encoding huPA was obtained by PCR using the following sense and nonsense primers:

5'-ATGCTAGATCTAATGAACTTCATCAGGTACCAT CG-3' (SEQ ID NO:1), and

5'-CGATAGATCTTTATTTTGACTTATCTATTTCAC AG-3' (SEQ ID NO:2).

Each of the above primers introduces a BglII site at the ends for cloning into the expression vector. Additionally, the sense strand primer introduces a KpnI site 14 nucleotides downstream from the signal peptide cleavage site, and the nonsense strand primer introduces a stop codon after Lys at position 48. The template DNA used was a clone of full length mature huPA in a yeast expression vector, as an alpha-factor fusion (pAB24UK300, consisting of the yeast shuttle vector pAB24 having a cassette inserted at the BamHI site, the cassette containing the ADH2-GAP hybrid promoter, the yeast ai-factor leader, the coding sequence for mature human uPA, and the GAP terminator, obtained from P. Valenzuela, Chiron Corporation) derived from a human kidney cDNA library (M. A. Truett et al., DNA (1985) 4:333–49). Polymerase chain reactions were carried out in 100 μL volumes with the following components: 10 mM Tris-HCl, pH 8.3, 50 mM KCl, 1.5 mM $MgCl_2$, 0.2 mM each dATP, dCTP, dGTP, and dTTP, 1 μM each primer, 9 ng template plasmid, and 2.5 U Taq DNA polymerase. The reaction conditions were 94° C. for 1 min, followed by 37° C. for 2 min, then 72° C. for 3 min, for 30 cycles. Both the PCR fragment and a subcloning vector (pCBR, described by Frederik et al., *J Biol Chem* (1990) 265:3793) containing the yeast expression cassette were digested with BglII and then ligated together, after treatment of the pCBR vector with alkaline phosphatase. Once the subclone was obtained (pCBRuPAα13), the expression cassette was isolated via BamHI digestion and ligated into the yeast shuttle vector (pAB24) to yield pAB24α13uPA1–48.

The expression plasmid was transformed into *Saccharomyces cerevisiae* AB110 (MATα leu2-3-112 ura3-52 pep4-3 [cir]°) using the lithium acetate method (Ito et al., *J Bacteriol* (1983) 153:163), and selected for uracil prototrophy. The plasmid copy number was then amplified by growth on minimal media without leucine, containing 8% glucose to keep ADH2-GAP promoter-mediated expression repressed. High level expression of secreted $huPA_{1-48}$ was obtained with pAB24α13uPA1–48 transformants of AB110 grown in leu medium and inoculating at 1:10 into YEP 4% glucose medium. All yeast cultures were grown at 30° C., 275 rpm, for 96 hours.

Example 2

(Purification of $huPA_{1-48}$)

One liter of yeast supernatant was harvested by centrifuging the cells at 2600×g. Protein was concentrated from the supernatant by adding 70% ammonium sulfate, incubating for 1 hr at 4° C., and separating the protein precipitate by centrifuging at 11,000×g for 1 hr at 4° C. The protein pellets were resuspended in buffer containing 20 mM potassium phosphate, pH 7.0, 50 mM NaCl, and 1 mM EDTA. The suspension was dialyzed against the same buffer, with two changes of 4 L, overnight at 4° C. The entire dialysate was loaded onto a 1.8 L SEPHADEX® G-50 column at room temperature. Fractions were collected and monitored with UV at 254 nm, then pooled based on 16% Tris-Tricine SDS-PAGE (Novex) under non-reducing conditions. The peak fractions, containing monomeric $huPA_{1-48}$, were then loaded onto a 22 mm C18 reverse phase HPLC column (Vydac) and the protein eluted with a 0.6% gradient of acetonitrile containing 1% TFA. The major peak eluting at 33.5 minutes was collected and lyophilized. The purification yield is summarized in Table 1:

TABLE 1

Purification of $huPA_{1-48}$

| Sample | Total Protein | Total Units[b] | Yield |
|---|---|---|---|
| Crude supernatant | ~200 mg[a] | 3.3 × 10⁶ | — |
| Ammonium sulfate | 160 mg | 2.0 × 10⁶ | 60% |
| G50 Column | 103 mg | 1.3 × 10⁶ | 42% |
| HPLC Purified | 8.4 mg | 7.4 × 10⁵ | 22% |

[a]Estimated protein concentration due to interference with BCA assay
[b]Unit = volume of crude sample required to inhibit binding of $^{125}$I-ATF 50% in competition with biotinylated suPAR.

Example 3

(Characterization of $huPA_{1-48}$)

Purified $huPA_{1-48}$ was subjected to amino acid analysis and N-terminal sequencing, yielding the expected composition and sequence. The Edman degradation was performed through residue 20. A stoichiometric amount of threonine was observed at cycle 18, indicating that this residue was not modified by fucosylation, as is found for uPA purified from eukaryotic cells. The absence of post translational modification was later confirmed by electrospray mass spectrometry. The binding activity of the recombinant $huPA_{1-48}$ was determined using a radio-receptor binding assay.

Baculovirus-derived recombinant human urokinase receptor was expressed as a truncated, soluble molecule as described previously for mouse L-cells (Masucci et al., *J Biol Chem* (1991) 266:8655). The purified receptor was biotinylated with NHS-biotin, and immobilized at 1 μg/mL in PBS/0.1% BSA on streptavidin coated 96-well plates. Human uPA ATF (residues 1–135, obtained from M. Shuman, University of California, San Francisco) was iodinated using the Iodogen method (Pierce), and used as tracer. The $^{125}$I-ATF was incubated at 100–500 pM with increasing amounts of $huPA_{1-48}$ in triplicate (100 pM-1 μM) for 2 hours at room temperature in 0.1% BSA/PBS in a total volume of 200 μL. The plates were then washed 3 times with PBS/BSA, and the remaining bound radioactivity determined. The apparent $K_d$ observed for $huPA_{1-48}$ was 0.3 nM, comparable to that reported for ATF and intact uPA.

Example 4

(Construction of huPA$_{1-48}$ Muteins)

In order to efficiently analyze the features of huPA$_{1-48}$, we performed a series of mutagenesis experiments utilizing phage display. Attempts to employ the system described by Scott and Smith, *Science* (1990) 249:386–90, were not successful. However, the use of monovalent phage display, using a phagemid and helper phage as described by Lowman et al., *Biochem* (1991) 30:10832–38, did result in functional display of the protein domain. Finally, we employed an affinity epitope "tag" to reduce the fraction of phage bearing only wild-type pIII protein, reducing the background in panning experiments.

A.) Construction of Phagemids:

The starting materials were a phagemid construct (pGMEGF) comprising a human epidermal growth factor (hEGF) gene linked to the lac promoter, using pBLUE-SCRIPT (Stratagene) as the backbone. The polylinker region of the vector contained within a PvuII fragment was replaced by a cassette comprising a leader sequence from the photo-bacterial superoxide dismutase fused to a synthetic gene for hEGF, in turn fused to residues 198–406 of the M13 pIII gene. The sequence of the insert is shown in SEQ ID NO:3. A synthetic gene encoding human urokinase residues 1–48 was obtained from J. Stratton-Thomas, Chiron Corporation.

Fusion proteins were generated using PCR. A first set of primers EUKMPCR1 and EUKGPCR1 were used with primer EUKPCR2 to add epitope tags to huPA$_{1-48}$ at the N-terminus, and to add an amber codon (TAG) and a BamHI site within residues 249–254 of the pIII protein at the C-terminus.

EUKMPCR1: CTCATCAAGCTTTAGCGGACTA-CAAAGACGAT

GACGATAAGAGC-AATGAACTTCATCAAG (SEQ ID NO:5);

EUKGPCR1: CTCATCAAGCTTTAGCCGAATACAT-GCCAATGG

AAAGCAATGAAC-TTCATCAAG (SEQ ID NO:6);

EUKPCR2: CACCGGAACCGGATCCAC-CCTATTTTGACTTATC (SEQ ID NO:7).

The PCR reactions yielded primary products of the expected sizes, 204 and 197 bp.

A second set of primers, SRO1 and EUKCPCR1, were used with the EGF-containing phagemid construct as template. These primers added a BamI site at pIII residues 250–251 and amplified a fragment ending at the unique Cla1 site at residues 297–299 of pIII.

SRO1: GAAATAGATAAGTCAAAATAGGGTG-GATCCGGT

TCCGGTGATTTTGATT-ATG (SEQ ID NO:8); and

EUKCPCR1: GAAACCATCGATAGCAGCACCG (SEQ ID NO:9).

This PCR reaction yielded a primary product of approximately 180 bp. The PCR reaction products were separated from unreacted primers by size exclusion chromatography (Chromaspin-100, Clontech), digested with restriction enzymes Hd3 and BamHI (set 1) or BamHI and Cla1 (set 2), and isolated from a 2.5% agarose gel, using the MERMAID procedure (Bio-101). Each of the set 1 fragments were ligated with the C-terminal reaction 2 fragment, the ligations digested with Hd3 and Cla1, and the resulting fragments ligated into pGMEGF (digested with Hd3 and Cla1, dephosphorylated with alkaline phosphatase). The ligations were transformed into *E. coli* JS5 (Biorad) by electroporation. Strain JS5 overproduces lac repressor, and is sup0, preventing expression of the uPA$_{1-48}$-pIII fusion protein due to the amber stop codon between the uPA$_{1-48}$ and pIII genes. Correct clones were identified by restriction analysis and confirmed by DNA sequencing. These steps yielded phagemids pHM1a (M1Flag-uPA$_{1-48}$) and pHM3a (Glutag-uPA$_{1-48}$). The DNA sequences of the fusion proteins in these phagemids are shown in SEQ ID NO: 10 and SEQ ID NO:12.

The phagemid containing a synthetic gene for uPA$_{1-48}$ was constructed in the same vector by the following steps. The sequence of the synthetic gene is shown in SEQ ID NO: 14. Plasmid pCBRuPA (16 μg), a derivative of pCBR (Frederick et al., *J Biol Chem* (1990) 265:3793) containing this synthetic gene for uPA$_{1-48}$, inserted between the yeast α-factor leader and GAPDH terminator as a BglII fragment, was digested with Sac1 and Cla1, and adapted for phagemid expression using the following set of synthetic oligonucleotides:

SRO35: AGCTTTAGCGGAATACATGCCAATG-GAAAGCAATGAGCT (SEQ ID NO: 16);

SRO36: CATTGCTTTCCATTGGCATGTATTC-CGCTAA (SEQ ID NO: 17);

SRO37: CGATAAGTCAAAATAGGGTG (SEQ ID NO: 18); and

SRO38: GATCCACCCTATTTTGACTTAT (SEQ ID NO: 19).

Oligonucleotides SRO36 and SRO37 (250 pmol) were phosphorylated with polynucleotide kinase and annealed with equimolar amounts of oligos SRO35 and SRO38, respectively. The two annealed duplexes (125 pmol) were ligated overnight with the digested plasmid DNA, the ligase heat inactivated, and the ends phosphorylated with polynucleotide kinase. The DNA was run on a 6% polyacrylamide gel and the correct sized band (ca. 200 bp) was excised and isolated. The insert was ligated with plasmid pHM1a (digested with Hd3 and BamHI) and phosphatased, and the ligations transformed into *E. coli* JS5. The correct recombinants were identified by restriction analysis, and confirmed by DNA sequencing, yielding phagemid pHM3-3.

B.) Production and Panning of Phagemids:

To produce phagemid particles, DNAs were transformed into *E. coli* strain XL1-BLUE (Stratagene) by electroporation. This strain was used because it is supE44 (TAG codon encodes Gln), laciQ (overproduces lac repressor), and makes phage (F'+). Overnight cultures were grown in 2×YT broth containing 50 μg/mL amnpicillin and 10 μg/mL tetracycline (to maintain the F'). Cells were diluted 1:50 or 1:100 into the same media, grown for 20 minutes as 37° C. for 10 minutes at 225 rpm to enhance phage attachment, and then grown with normal agitation at 325 rpm overnight. Phage particles were then purified and concentrated by two successive precipitations with polyethylene glycol. The concentrations of phage present were determined by infection of *E. coli* XL1-blue and plating on L broth plates containing 50 μg/mL ampicillin.

To pan for binding phage particles, small tissue culture plates were coated either with anti-Glu antibody (R. Clark, Onyx Corporation) or streptavidin at 10 μg/mL in PBS overnight. Plates were then blocked with PBS containing 0.1% BSA. To the streptavidin plates was then added 1 μg/mL of biotinylated secreted human urokinase receptor obtained by recombinant baculovirus infection of *A. californica* Sf9 cells. After 2 hours at room temperature, the plates were again blocked with BSA, and phage ($10^6$–$10^{10}$ cfu) were added in 1 mL of PBS/BSA. After incubation for 1 hour, non-specifically adhered phage were removed by washing (7×1 mL PBS/BSA), and the remaining phage eluted with 1 mL of 0.1 M glycine, pH 2.2, for 30 minutes. The eluted phage were immediately neutralized with 1 M Tris, pH 9.4, and stored at 4° C. overnight. The number of phage eluted was determined by titering on *E. coli* XL1-blue on ampicilflin plates. The procedure, where phage are first bound and eluted from the Glu-Ab plates and then panned against receptor plates, reduces the high background that would otherwise result from the large number of phage containing only wild type pIII: only phage containing an insert in pIII display an epitope tag and are selected on anti-Glu MAbs plates.

Table 2 shows that phagemids displaying uPA$_{1-48}$ are specifically bound and eluted from immobilized urokinase receptor. Table 3 demonstrates that the phagemid which displays a Glu tag-uPA$_{1-48}$ fusion is specifically retained by immobilized Glu Ab. Finally, Table 4 shows that a population of the Glu-uPA$_{1-48}$ phagemid which has been specifically eluted from the Glu Ab plates, is retained with a much higher yield on urokinase receptor plates, than is the unenriched phagemid population.

TABLE 2

Panning on Immobilized Receptor

| | | | % Yield | |
|---|---|---|---|---|
| Sample | Phage/phagemid | Input[e] | −uPAR | +uPAR |
| 1[a] | 1a | 9.4 × 10$^9$ | 0.0018 | 0.094 |
| 2[b] | 3a | 1.4 × 10$^{10}$ | 0.0014 | 0.08 |
| 3[c] | pGMEGF | 1.3 × 10$^{10}$ | 0.0015 | 0.0012 |
| 4[d] | LP67 (control) | 1.4 × 10$^9$ | — | 0.0099 |

[a]M1-FLAG-UPAELD-short pIII (pHM1a)
[b]Glu-tag-UPAELD-short pIII (pHM3a)
[c]M1-FLAG-EGF-medium long pIII (pGMEGF)
[d]LP67-control phage (Amp$^r$ M13)
[e]ampicillin resistant colonies, in cfu

TABLE 3

Panning phage with Glu-Ab or suPAR

| | | | % Yield | |
|---|---|---|---|---|
| Sample | Phage/phagemid | Input[a] | suPAR[b] | GluAb |
| 1 | pHM1a | 1.5 × 10$^{10}$ | 0.55% | 0.003% |
| 2 | pHM3a | 2.5 × 10$^{10}$ | 0.44% | 0.048% |
| 3 | LP67 (control) | 3.5 × 10$^5$ | 0.008% | — |

[a]ampicillin resistant colonies, in cfu
[b]soluble uPA receptor

TABLE 4

Panning GluAb-unenriched and enriched phage on suPAR

| | | | % Yield | |
|---|---|---|---|---|
| Sample | Phage/phagemid | Input[a] | suPAR[b] | GluAb |
| 1 | pHM3a | 2.7 × 10$^7$ | 0.85% | 0.08% |
| 2 | pHM3a (enriched) | 6 × 10$^6$ | 9.7% | 3.3% |
| 3 | LP67 (control) | 5.4 × 10$^6$ | <0.04% | <0.02% |

[a]ampicillin resistant colonies, in cfu
[b]soluble uPA receptor

These enriched phagemid pools are used for multiple mutagenesis strategies in order to identify improved uPA$_{1-48}$ ligands with altered specificity or improved affinity. For example the region between residues 13 and 32 of human uPA has been implicated in receptor binding (E. Appella et al., *J Biol Chem* (1987) 262:4437–40). Key residues in the region from 19–30 can be easily mutated by replacing the region between the unique restriction sites Kpnl and Munl.

In order to rapidly and quantitatively assess the binding affinities of the resulting uPA$_{1-48}$ variants, relatively large quantities of properly folded proteins are required. Although this could be done by bacterial expression, using the phagemid constructs in a sup0 strain and inducing with IPTG, such a strategy yields relatively small amounts of protein in the periplasm. A second strategy is to express the variants in yeast, as described above for the wild type protein. To accomplish this we have constructed a yeast expression vector which enables us to move fragments encoding residues 4–48 of uPA$_{1-48}$ in a single step from the phagemid vectors. This was accomplished as follows: Plasmid pAGαG, identical to pCBR except for a small deletion of an Xba fragment in the ADH2-GAPDH promoter, was digested with Sac1, which cleaves once within the promoter, and then treated with Mung Bean nuclease which destroys the site. Subsequent religation yielded plasmid pAGαG-Sac. Digestion with BglII and treatment with alkaline phosphatase yielded a vector into which was ligated the BglII fragment corresponding to the synthetic gene for uPA$_{1-48}$. Transformation of *E. coli* strain HB101 to ampicillin resistance and restriction analysis yielded the correct clone. The 2.4 kB BamHI fragment from this plasmid (pAGαG-Sac1-48synth), containing the expression cassette, was isolated and ligated into pAB24, which had been treated with BamHI and alkaline phosphatase. The resulting plasmid has unique Sac1 and Xhol sites which can be used for transfer of the phagemid 1–48 genes. This is accomplished by digesting the phagemid with BamHI, treating with Mung Bean Nuclease, digesting with Sac1 and isolating the 145 bp fragment. The vector is digested with Xhol, treated with Mung Bean Nuclease, digested with Sac1, and treated with alkaline phosphatase. Ligation then yields the correct recombinants in a single step in the yeast expression vector. Transformation of yeast strain AB110 then yields high levels of secreted 1–48 variants for analysis.

Using this construct, one can express a library of uPA variations for screening. Variations may be constructed by a variety of methods, including low-fidelity PCR (which introduces a large number of random point mutations), site-specific mutation, primer-based mutagenesis, and ligation of the uPA$_{1-48}$ sequence (or portions thereof) to a random oligonucleotide sequence (e.g., by attaching (NNS)$_x$ to the uPA$_{1-48}$ coding sequence, or substituting NNS for one or more uPA$_{1-48}$ codons). Generation of random oligonucleotide sequences is detailed in Devlin, WO91/18980, incorporated herein by reference. Phage displaying uPA$_{1-48}$ variants (having one or more amino acid substitutions) are screened according to the protocol described above (using, e.g., pHM3a as a positive control) and selected for improved binding.

Example 5

(Formulation of huPA$_{1-48}$)

huPA$_{1-48}$ formulations suitable for use in chemotherapy are prepared as follows:

A) Injectable Formulation:

| | |
|---|---|
| huPA$_{1-48}$ | 7.0 mg |
| Na$_2$HPO$_4$ (0.5 M) | 0.5 mL |
| mannitol (25%) | 2.5 mL |
| sodium laureate (1%) | 2.5 mL |
| pH | 7.5 |
| PBS qs | 20 mL |

This formulation is prepared following the procedure set forth in U.S. Pat. No. 4,816,440, incorporated herein by reference. The formulation is administered by parenteral injection at the site to be treated. The formulation is also generally suitable for administration as eyedrops directly to the conjunctiva, or by intranasal administration as an aerosol. Alternatively, a concentrated formulation (e.g., reducing the phosphate buffered saline to 2 mL) may be used to fill an ALZET® minipump, and the minipump implanted at the site to be treated.

| B) Ophthalmic Preparation: | |
|---|---|
| $huPA_{1-48}$ | 1 mg |
| fibronectin | 69 mg |
| albumin | 37.5 mg |
| water qs | 3.0 mL |
| HCl (0.01 M) qs | pH 4.0 |

This dosage form is prepared following the procedure set forth in U.S. Pat. No. 5,124,155, incorporated herein by reference. The fibronectin and albumin are dissolved in water to form a 3.0 mL solution, and HCl added to a pH of 4.0, causing the fibronectin to flocculate. The flocculent is filtered, and combined with the $huPA_{1-48}$. The mixture is then placed in a contact lens mold, and the mold closed for 30 min to form a corneal "shield" in the shape of a contact lens. The shield releases $huPA_{1-48}$ over a period of time, and is useful for preventing angiogenesis of corneal tissue following ophthalmic surgery.

The present invention has been described with reference to specific embodiments. However, this application is intended to cover those changes and substitutions which may be made by those skilled in the art without departing from the spirit and the scope of the appended claims.

What is claimed is:

1. A method for treating a urokinase-type plasminogen activator (uPA)-mediated disorder, said method comprising:
   (i) providing a composition comprising a non-fucosylated polypeptide consisting essentially of huPA$_{1-18}$ or an active peptide analog thereof, wherein said active peptide analog is a polypeptide differing from the sequence of huPA$_{4-18}$ by one to seven amino acids, which possesses substantially the same or greater binding affinity to huPAR as huPA$_{4-18}$, and
   (ii) administering an effective amount of said composition to a patient having a uPA-mediated disorder.

2. The method of claim 1, wherein said uPA-mediated disorder is selected from the group consisting of metastasis, inappropriate angiogenesis, and chronic inflammation.

3. The method of claim 1, wherein said uPA-mediated disorder is selected from the group consisting of Kaposi's sarcoma, diabetic retinopathy, and rheumatoid arthritis.

4. The method of claim 1, wherein said composition is administered by instillation in the eye.

5. The method of claim 1, wherein said uPA-mediated disorder is metastasis.

6. The method of claim 1, wherein said uPA-mediated disorder is inappropriate angiogenesis.

7. The method of claim 6, wherein said inappropriate angiogenesis is corneal angiogenesis.

8. The method of claim 1, wherein said uPA-mediated disorder is chronic inflammation.

9. The method of claim 1, wherein said uPA-mediated disorder is Kaposi's sarcoma.

10. The method of claim 1, wherein said uPA-mediated disorder is diabetic retinopathy.

11. The method of claim 1, wherein said uPA-mediated disorder is rheumatoid arthritis.

12. The method of claim 1, wherein said polypeptine is huPA$_{1-48}$.

13. The method of claim 1, wherein said polypeptide possesses a $K_d$ of about 0.3 nM.

* * * * *